(12) United States Patent
Heyoung

(10) Patent No.: US 9,248,207 B1
(45) Date of Patent: Feb. 2, 2016

(54) ELECTRON MICROSCOPE PLASMA CLEANER

(71) Applicant: Hitachi High-Technologies Korea Co., Ltd., Seoul (KR)

(72) Inventor: Heyoung Cheol Heyoung, Gyeonggi-do (KR)

(73) Assignee: Hitachi High-Technologies Korea Co., Ltd. (KR)

( * ) Notice: Subject to any disclaimer, the term of this patent is extended or adjusted under 35 U.S.C. 154(b) by 0 days.

(21) Appl. No.: 14/495,580

(22) Filed: Sep. 24, 2014

(30) Foreign Application Priority Data

Sep. 3, 2014 (KR) .......................... 10-2014-116933

(51) Int. Cl.
*H01J 37/00* (2006.01)
*A61L 2/14* (2006.01)
*H01J 37/10* (2006.01)
*H01J 37/26* (2006.01)

(52) U.S. Cl.
CPC . *A61L 2/14* (2013.01); *H01J 37/10* (2013.01); *H01J 37/261* (2013.01); *H01J 2237/10* (2013.01); *H01J 2237/2602* (2013.01)

(58) Field of Classification Search
CPC .......... A61L 2/14; H01J 37/10; H01J 37/261; H01J 2237/10; H01J 2237/2602
USPC ................... 250/306, 307, 310, 311
See application file for complete search history.

(56) References Cited

U.S. PATENT DOCUMENTS 6,610,257 B2 * 8/2003 Vane .......................... 422/186.04
2007/0284541 A1 * 12/2007 Vane .......................... 250/441.11

FOREIGN PATENT DOCUMENTS

JP 2005-197467 A 7/2005
KR 10-2010-0023080 A 3/2010

* cited by examiner

*Primary Examiner* — Michael Maskell
(74) *Attorney, Agent, or Firm* — Akerman LLP

(57) ABSTRACT

The present invention relates to an electron microscope plasma cleaner for cleaning an electron microscope by using plasma, the cleaner including a vacuum chamber in which the sample is disposed; an electron gun for producing the electron beam and outputting the produced electron beam to the sample; an electron lens for magnifying the electron beam transmitting the sample and projecting the electron beam onto a fluorescent screen; a radio frequency controller for producing a first signal having radio frequency within a given range; and a plasma head for producing the plasma, receiving the first signal from the radio frequency controller, producing activated oxygen radicals and ions by using the plasma and the first signal, and supplying the activated oxygen radicals and ions to the interior of the vacuum chamber.

6 Claims, 20 Drawing Sheets

FIG. 16b
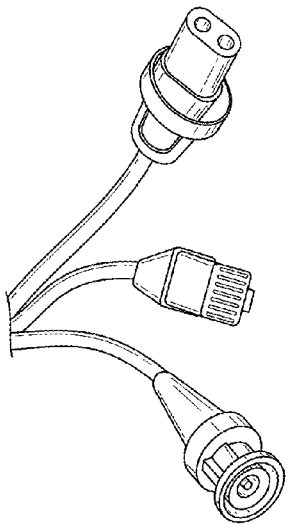
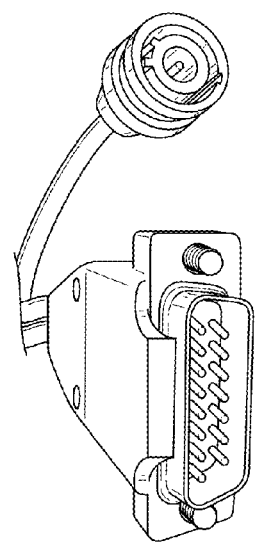
FIG. 16c
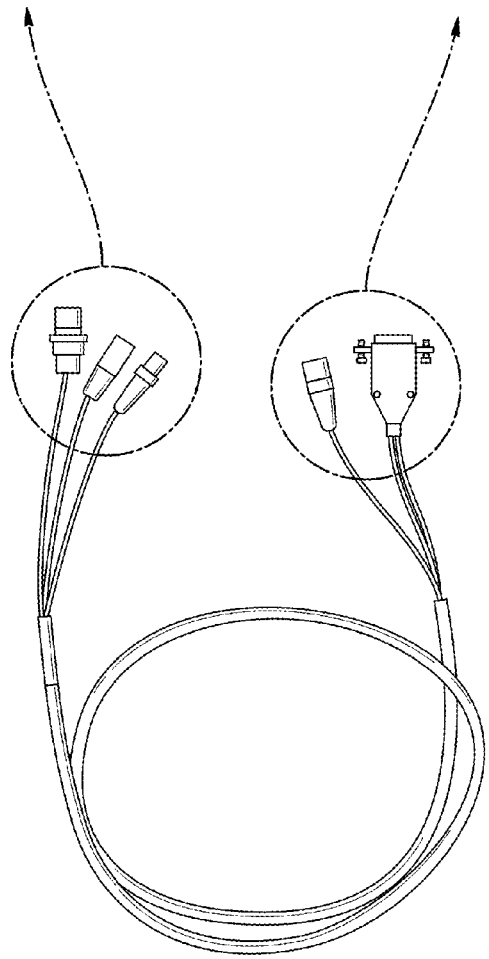
FIG. 16a

ELECTRON MICROSCOPE PLASMA CLEANER

CROSS-REFERENCE TO RELATED APPLICATIONS

The present application claims priority to Korean Patent Application No. 10-2014-116933, filed Sep. 3, 2014, the entirety of which is incorporated herein by reference.

BACKGROUND OF THE INVENTION

1. Field of the Invention

The present invention relates to an electron microscope plasma cleaner that has a triple plasma electrode and a multi gas injection nozzle, thus achieving the effective generation of plasma, and more particularly, to an electron microscope plasma cleaner that cleans the interior of a chamber of an electron microscope and the surface of a sample of the electron microscope with the radicals and ions produced by means of plasma, thus achieving the improvements in high resolution image observation and precision length measurement of the electrode microscope and the pattern distortion and damage of the image observed through the electrode microscope.

2. Background of the Related Art

An electron microscopes, which collects an electron beam and produces a focus thereon to observe and analyze the surface and interior of a sample, includes a scanning electron microscope (SEM), a critical dimension-scanning electron microscope (CD-SEM), a transmission electron microscope (TEM), dual beam (SEM+FIB (focused ion beam)), a nano prober and so on.

The electron microscope is a device that produces a high density electron current from an electron gun, collects an electron beam in an electron column, forms a focus thereon, radiates the electron beam onto a local observation point of a sample to be analyzed, produces and detects a signal, and magnifies (tens to millions of times) the image on the surface and interior of the sample.

With the development of nano technology, the electron microscope becomes necessary equipment for research, manufacturing process and quality management in all kinds of industrial fields like semiconductors, advanced materials, displays and so on.

On the other hand, cleaning organics and native oxide existing on the interior of a vacuum chamber of the electron microscope and the surface of a sample becomes a serious problem.

That is, the contamination caused by the organics on the vacuum chamber of the electron microscope and the surface of the sample gives bad interference in the observation of the image of the electron microscope, thus undesirably causing the contamination and deformation of the observed region and providing main interference in the spatial resolution like noise increment of the image.

The contamination on the vacuum chamber of the electron microscope is caused by the outgas from a photo resist as a main material of a semiconductor process and an organic material having high permittivity and weak bonding characteristics.

Further, the contamination of the vacuum chamber is caused by the contaminants of various structures (a sample stage, a sample holder and so on) of the vacuum chamber and the out-gas from grease.

Such organics have heavy mass and low motion energy, and accordingly, since most of organics are not pumped by means of a vacuum pump, they are absorbed/desorbed in the vacuum chamber and randomly move to collide against the beam incident thereon, thus being positively ionized. Further, the positive ions are deposited onto the area of the sample to which the electron beam is radiated having high negative charges therearound to form a black organic ion deposited film, which decreases the resolution of the image or deforming the observed pattern, thus making it hard to achieve accurate observation or fine measurement.

Further, the contamination of the organics on the surface of the sample is caused by various kinds of chemicals used for making the sample, residues reacting to the chemicals, water remaining after washing, and oil and water of a user' body.

When the sample is kept in the air, further, native oxide is formed thereon to cause the surface of the sample to be contaminated.

If the contaminated sample is introduced into the sample chamber to observe the image of the electron microscope, the pattern distortion and the reduction of resolution of the observed image may become serious.

So as to solve the above-mentioned problems, accordingly, there is a definite need for the development of a new electron microscope plasma cleaner.

SUMMARY OF THE INVENTION

Accordingly, the present invention has been made in view of the above-mentioned problems occurring in the prior art, and it is an object of the present invention to provide an electron microscope plasma cleaner that has a triple plasma electrode and a multi gas injection nozzle, thus achieving the effective generation of plasma.

It is another object of the present invention to provide an electron microscope plasma cleaner that cleans the interior of a chamber of an electron microscope and the surface of a sample of the electron microscope with the radicals and ions produced by means of plasma, thus achieving the improvements in the high resolution image observation and precision length measurement in the electrode microscope and the pattern distortion and damage of the image observed through the electrode microscope.

To accomplish the above-mentioned objects, according to a first aspect of the present invention, there is provided an electron microscope plasma cleaner for cleaning an electron microscope by using plasma, the electron microscope adapted to magnify an image of a sample through an electron beam, the electron microscope plasma cleaner including: a vacuum chamber in which the sample is disposed, the interior of the vacuum chamber being in a vacuum state to utilize electron current; an electron gun for producing the electron beam and outputting the produced electron beam to the sample; an electron lens for magnifying the electron beam transmitting the sample and projecting the electron beam onto a fluorescent screen; a radio frequency controller for producing a first signal having radio frequency within a given range; and a plasma head for producing the plasma, receiving the first signal from the radio frequency controller, producing activated oxygen radicals and ions by using the plasma and the first signal, and supplying the activated oxygen radicals and ions to the interior of the vacuum chamber, wherein contaminants existing in the interior of the vacuum chamber are removed with the activated oxygen radicals and ions supplied to the interior of the vacuum chamber.

According to the present invention, desirably, the contaminants include hydrocarbons, native oxide formed when the sample is kept in the air, oil, and sample outgas.

According to the present invention, desirably, at least one of the activated oxygen radicals and ions reacts to the contaminants to produce $H_2O$ or $CO_2$.

According to the present invention, desirably, the motion energy of the contaminants becomes high by means of the production of $H_2O$ or $CO_2$, so that the contaminants are discharged to the outside of the vacuum chamber by means of the pumping operation of a vacuum pump.

According to the present invention, desirably, the ions supplied to the interior of the vacuum chamber are bonded to static electricity formed on the vacuum chamber and the sample, thus removing the static electricity.

According to the present invention, desirably, the electron microscope includes a transmission electron microscope (TEM), a scanning electron microscope (SEM), a scanning transmission electron microscope (STEM), and an X-ray micro analyzer (EFMA or XMA).

According to the present invention, desirably, the vacuum chamber includes a sample chamber (SC) and a sample exchange chamber (SEC).

According to the present invention, desirably, the plasma head includes a plasma electrode having a plurality of cups laid on each other, each cup having a plurality of holes formed on every surface thereof, so that the reaction area with a first gas producing the plasma is maximized through the plurality of cups and the plurality of holes.

According to the present invention, desirably, the plasma head includes a multi gas injection nozzle disposed on the front surface thereof to inject the first gas therefrom, thus assisting the production of the plasma.

To accomplish the above-mentioned objects, according to a second aspect of the present invention, there is provided a method for cleaning an electron microscope by using plasma, the electron microscope adapted to magnify an image of a sample through an electron beam, the method including the steps of: disposing the sample in an interior of a vacuum chamber being in a vacuum state to utilize electron current; producing the electron beam through an electron gun; outputting the produced electron beam to the sample; magnifying the electron beam transmitting the sample through an electron lens and projecting the electron beam onto a fluorescent screen; producing a first signal having radio frequency within a given range from a radio frequency controller; producing the plasma through a plasma head; receiving the first signal from the radio frequency controller through the plasma head; producing activated oxygen radicals and ions from the plasma head by using the plasma and the first signal; and supplying the activated oxygen radicals and ions from the plasma head to the interior of the vacuum chamber, wherein contaminants existing in the interior of the vacuum chamber are removed with the activated oxygen radicals and ions supplied to the interior of the vacuum chamber.

According to the present invention, desirably, the contaminants include hydrocarbons, native oxide formed when the sample is kept in the air, oil, and sample outgas.

According to the present invention, desirably, at least one of the activated oxygen radicals and ions reacts to the contaminants to produce $H_2O$ or $CO_2$.

According to the present invention, desirably, the motion energy of the contaminants becomes high by means of the production of $H_2O$ or $CO_2$, so that the contaminants are discharged to the outside of the vacuum chamber by means of the pumping operation of a vacuum pump.

According to the present invention, the method includes the step of bonding the ions supplied to the interior of the vacuum chamber to static electricity formed on the vacuum chamber and the sample and removing the static electricity.

According to the present invention, desirably, the electron microscope includes a transmission electron microscope (TEM), a scanning electron microscope (SEM), a scanning transmission electron microscope (STEM), and an X-ray micro analyzer (EFMA or XMA), and the vacuum chamber includes a sample chamber (SC) and a sample exchange chamber (SEC).

BRIEF DESCRIPTION OF THE DRAWINGS

The above and other objects, features and advantages of the present invention will be apparent from the following detailed description of the preferred embodiments of the invention in conjunction with the accompanying drawings, in which:

FIGS. 16a to 16c show a cable set according to the present invention;

DETAILED DESCRIPTION OF THE PREFERRED EMBODIMENTS

Hereinafter, an explanation on an electron microscope plasma cleaner according to the present invention will be in detail given with reference to the attached drawing.

Figure 1:
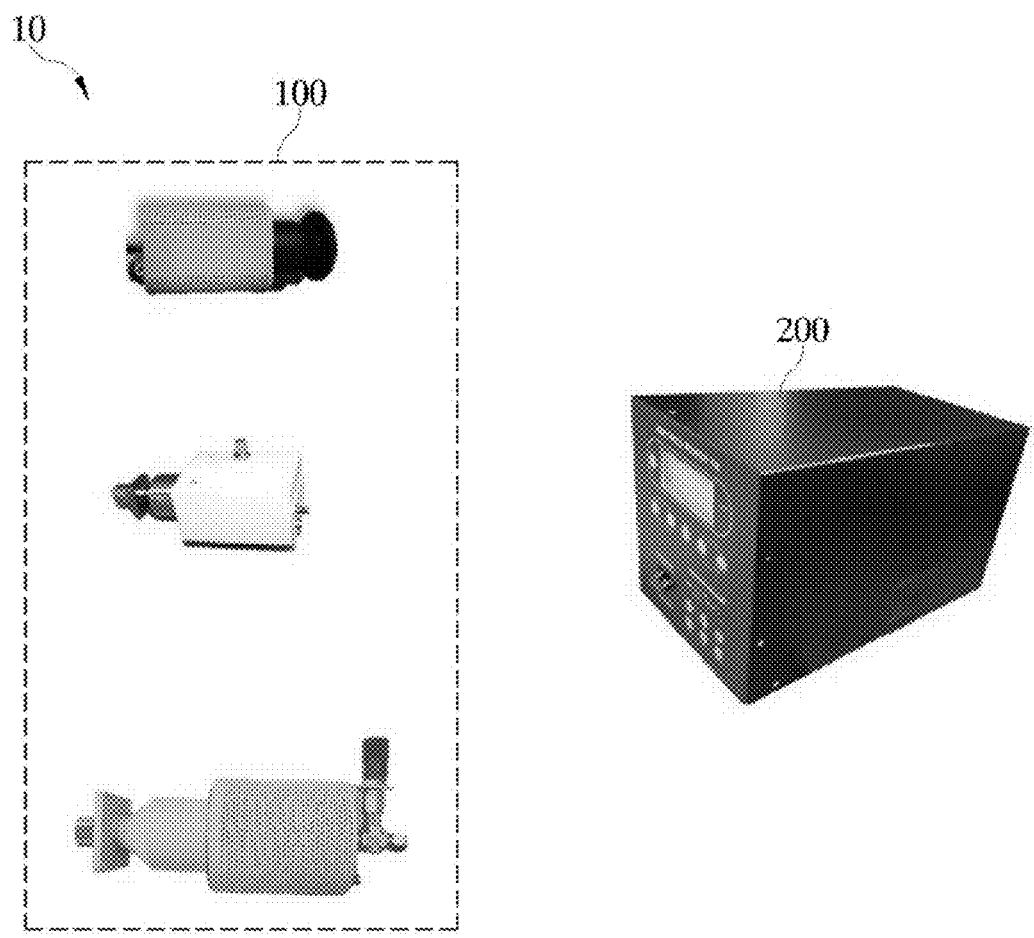
FIG. 1 shows an electron microscope plasma cleaner according to a first embodiment of the present invention.

FIG. 1 shows an electron microscope plasma cleaner according to a first embodiment of the present invention.

Referring to FIG. 1, an electron microscope plasma cleaner 10 according to a first embodiment of the present invention largely includes a plasma head 100 and a plasma controller 200.

The plasma head 100 as shown in FIG. 1 may include a sample exchange chamber (SEC)-mounted type plasma head, a sample chamber (SC)-mounted type plasma head, and an SEC and SC-mounted type plasma head.

As mentioned above, cleaning the organics and native oxide on the interior of a vacuum chamber of an electron microscope and the surface of a sample becomes a serious problem.

That is, the contamination caused by the organics on the vacuum chamber and the surface of the sample gives bad interference in the observation of the image of the electron microscope, thus undesirably causing the contamination and deformation of the observed region and providing a main interference in the spatial resolution like the noise increment of the image.

Figure 2:
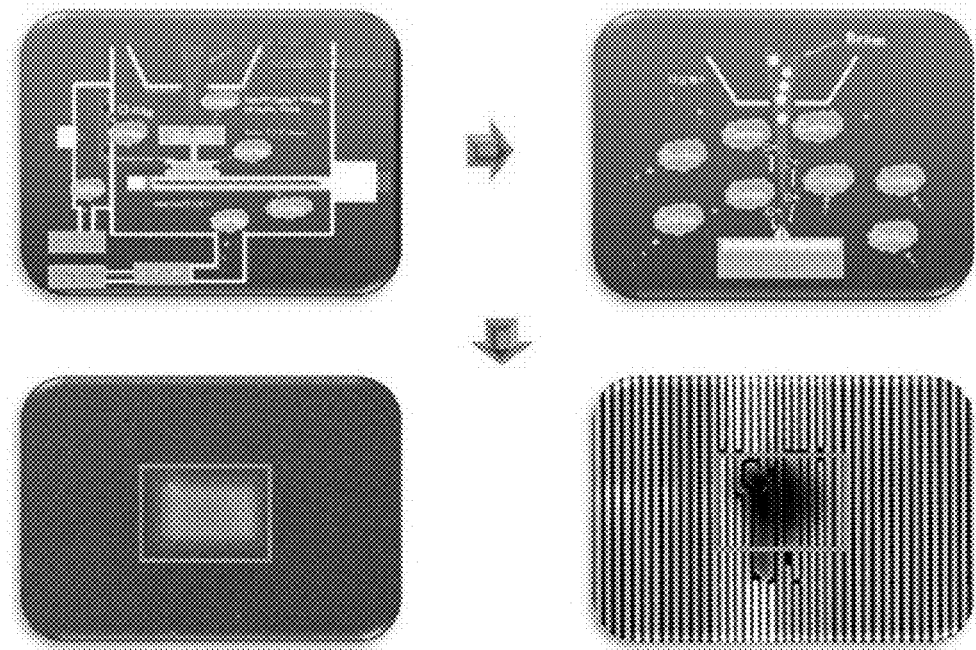
FIG. 2 shows the contamination of a sample chamber of an electron microscope.

FIG. 2 shows the contamination of a sample chamber of an electron microscope.

Referring to FIG. 2, organic molecules like hydro carbons in the scanning electron microscope (SEM) sample chamber and an electron beam collide against each other to produce positive ions, and the produced positive ions are deposited to reduce the resolution and further cause image interference like pattern damage and shrinkage.

Figure 3:
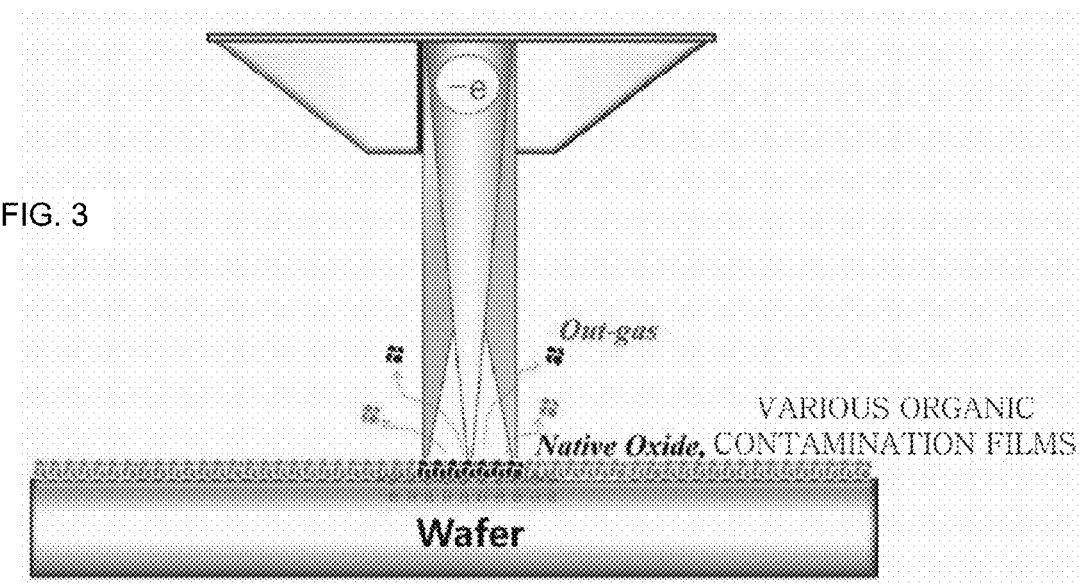
FIG. 3 shows the principle related to the image interference caused by the contamination on the surface of the sample chamber of the electron microscope.

FIG. 3 shows the principle related to the image interference caused by the contamination on the surface of the sample chamber of the electron microscope.

Referring to FIG. 3, native oxide and various organic contamination films are formed on a wafer, thus undesirably causing the malfunctions of the device and the performance reduction.

In more detail, surface native oxide, all kinds of organic contaminants, sample material out-gas, hydrocarbons absorbed on a scanning area (which remove a square contaminated area), and residual chemicals on the surface of the sample after pre-treatment are formed on the wafer.

So as to solve the above-mentioned problems, accordingly, the electron microscope plasma cleaner according to the present invention has a triple plasma producing electrode and a multi gas injection nozzle, thus effectively producing plasma. In more detail, the interior of the chamber of the electrode microscope and the surface of the sample of the electrode microscope are cleaned by means of the radicals and ions produced by plasma, thus achieving the improvements in the high resolution image observation and precision length measurement in the electrode microscope and the pattern distortion and damage.

According to present invention, after oxygen radicals are produced by using low power plasma (<30 W), if the produced oxygen radicals flow into the chamber of the electrode microscope, the native oxide and organic contaminants on the surface of the sample are removed, and the hydrocarbons staying in the chamber, without being pumped, are bonded to the oxygen radicals, so that the hydrocarbons are activated to gas such as $CO_2$ and $H_2O$ and then removed by means of a vacuum pump.

According to the present invention, the electron microscope plasma cleaner can remove hydrocarbons, native oxide, oil, sample outgas, and all kinds of organic contaminants on the SEM observation area which cause the contamination in the vacuum chamber of an analyzer such as SEM, TEM, FIB, dual beam and the like by using plasma.

First, low power RF (13.56 MHz/10~30 W) is applied to a high efficiency plasma source (triple plasma source) mounted on the vacuum chamber of the analyzer, thus producing activated oxygen radicals and ions through plasma.

Such oxygen radicals and ions move in the pumping direction in the vacuum chamber of the SEM. At this time, the oxygen radicals and ions react to heavy organic molecules (hydrocarbons: HnCn) whose motion energy is low and chemically bonded and activated to gas such as $H_2O$ or $CO_2$, and accordingly, the motion energy of the organic molecules become high, and the organic molecules are pumped and removed by means of the vacuum pump.

Further, static electricity (charging) existing on the sample on a semiconductor wafer or LCD and the chamber structure causing various defects is injected through the production of positive ions, and accordingly, the static electricity (charging) is bonded to charged electrons and removed, thus providing excellent removal of the static electricity. The electron microscope plasma cleaner includes a low power RF generator, a matching controller (auto and manual), a plasma source (triple cup plasma source) mounted on the vacuum chamber of the electron microscope, and a vacuum gauge. The operation of the electron microscope plasma cleaner is very conveniently conducted in one touch manner by means of an operator.

Figure 4:
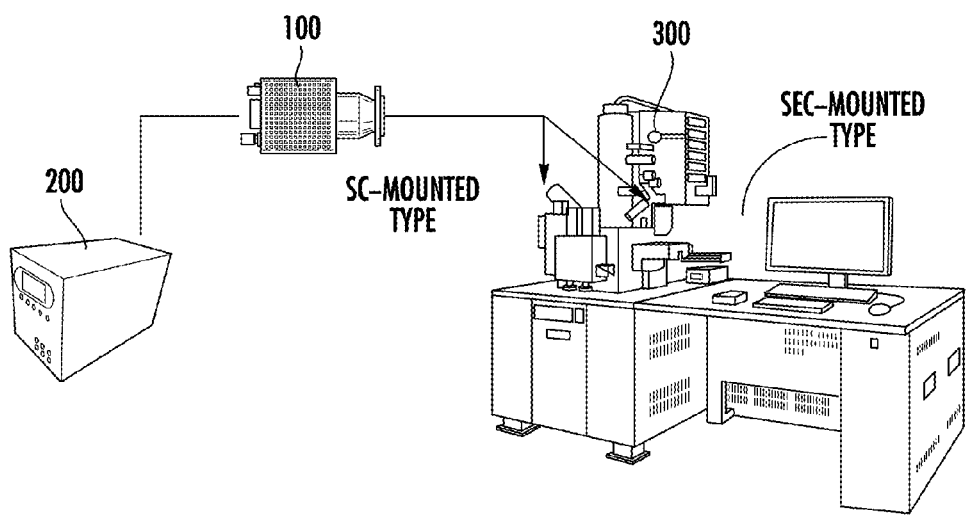
FIGS. 4 and 5 show an electron microscope plasma cleaner according to a second embodiment of the present invention.
Figure 5:
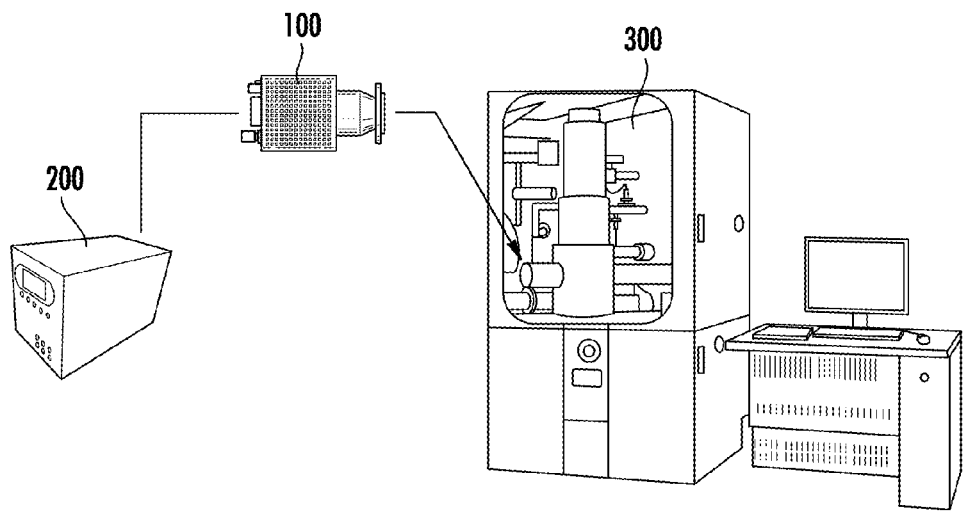

FIGS. 4 and 5 show an electron microscope plasma cleaner according to a second embodiment of the present invention.

Referring to FIG. 4, after oxygen radicals and ions are produced by using low power plasma (<30 W), if the produced oxygen radicals and ions flow into the chamber of the electrode microscope, the hydrocarbons staying in the chamber, without being pumped, are bonded to the oxygen radicals and activated to gas such as $CO_2$ and $H_2O$. After that, the gas is removed by means of a vacuum pump. The electron microscope plasma cleaner according to the second embodiment of the present invention may be mounted on the sample chamber and the sample exchange chamber.

In FIG. 5, in-lens type SEM introduces a side entry holder, which is mounted just on the sample chamber.

Figure 6:
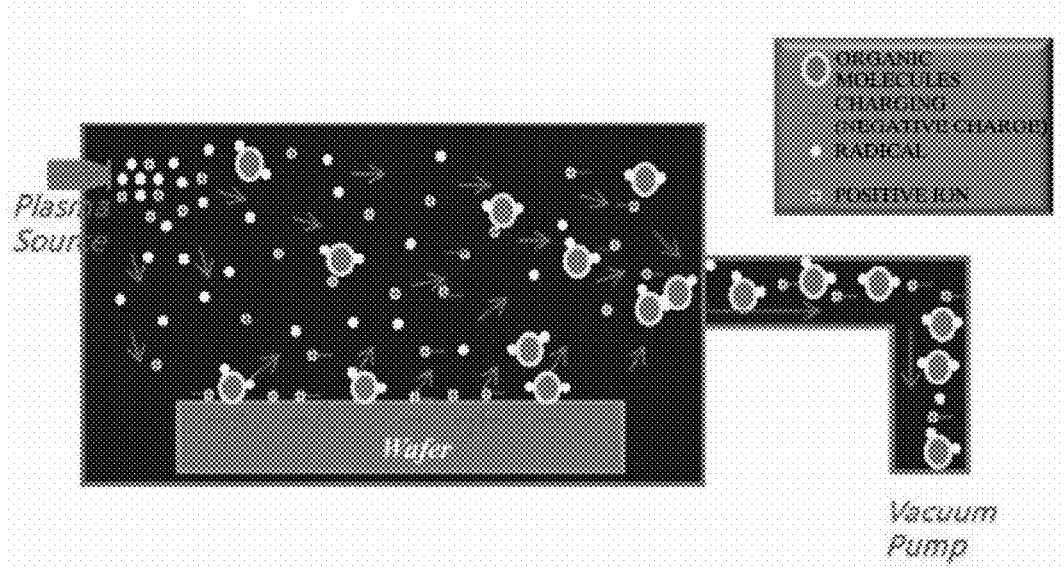
FIG. 6 shows the plasma cleaning performance according to the present invention.

On the other hand, FIG. 6 shows the plasma cleaning performance according to the present invention.

Referring to FIG. 6, the step of removing the beam contaminants in the equipment using electron beam and ion beam is shown.

Further, native oxide, hydrocarbons and organic contaminants are removed from the surface of the sample.

Furthermore, the pattern distortion caused by the contaminants is improved.

Additionally, the ultra high resolution of SEM/FIB is obtained.

Also, the charging (static electricity) existing on the wafer, liquid crystal or chamber structure of the in-line equipment of semiconductors or LCDs is removed to improve the defective rate.

Further, quantities of carbon and oxide detected in the vacuum chamber upon the EDXS analysis are improved to reduce the pattern shrinkage of the semiconductor sample.

Figure 7:
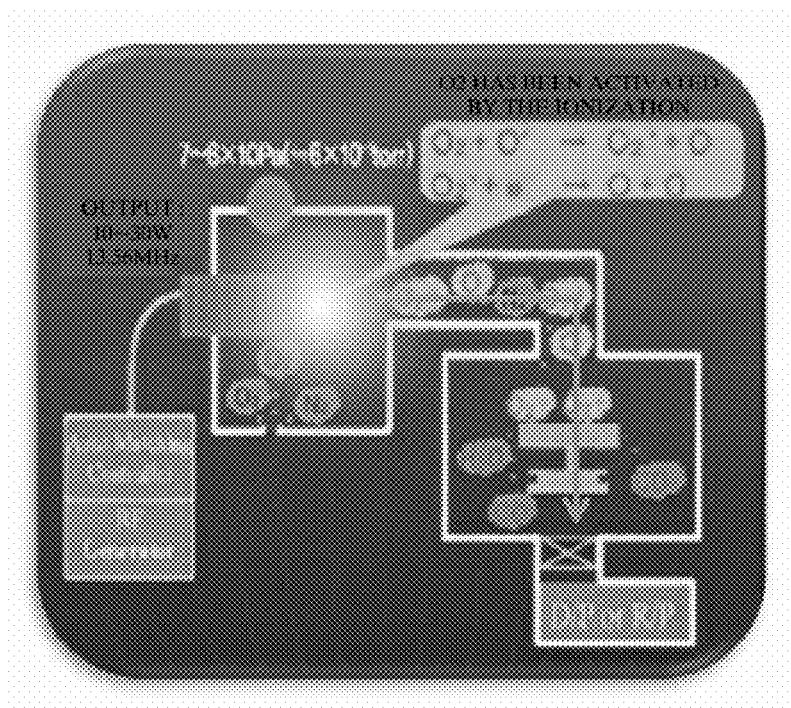
FIG. 7 shows the cleaning effects according to the mounting types of the electron microscope plasma cleaner according to the present invention.

FIG. 7 shows the cleaning effects according to the mounting types of the electron microscope plasma cleaner according to the present invention.

Referring to FIG. 7, a radio frequency RF (13.56 MHz/~40 W) as a standard of a semiconductor device is applied to the triple plasma source mounted on the vacuum chamber of the cleaner having the configuration of FIG. 6, thus producing oxygen radicals.

Further, if the oxygen radicals flow into the chamber, all kinds of contaminants on the surface of the sample, which cause image interference, are bonded to the oxygen radicals and activated to gas such as $CO_2$, $H_2O$, and $O_2$. After that, the gas is introduced and removed by means of a vacuum pump.

In this case, all kinds of organics, oxide, outgassing sample membrane, chemical residues and the like are removed.

As a result, the contaminants on the surface of the wafer (or sample) of the FE-SEM are cleaned through plasma, thus achieving the improvements in the high resolution image observation, the point distortion caused by electron-beam damage, and the accuracy of the pattern shrinkage EDXS composition analysis.

Accordingly, the electron microscope plasma cleaning according to the present invention can provide the achievement of ultra high resolution, the improvement of voltage contrast, the minimization of sample damage, the improvement of pattern shrinkage, and the high accuracy of EDXS analysis.

Hereinafter, the cleaning steps and configurations of the electron microscope plasma cleaner according to the present invention will be explained with reference to FIGS. 8 to 13.

Figure 8:
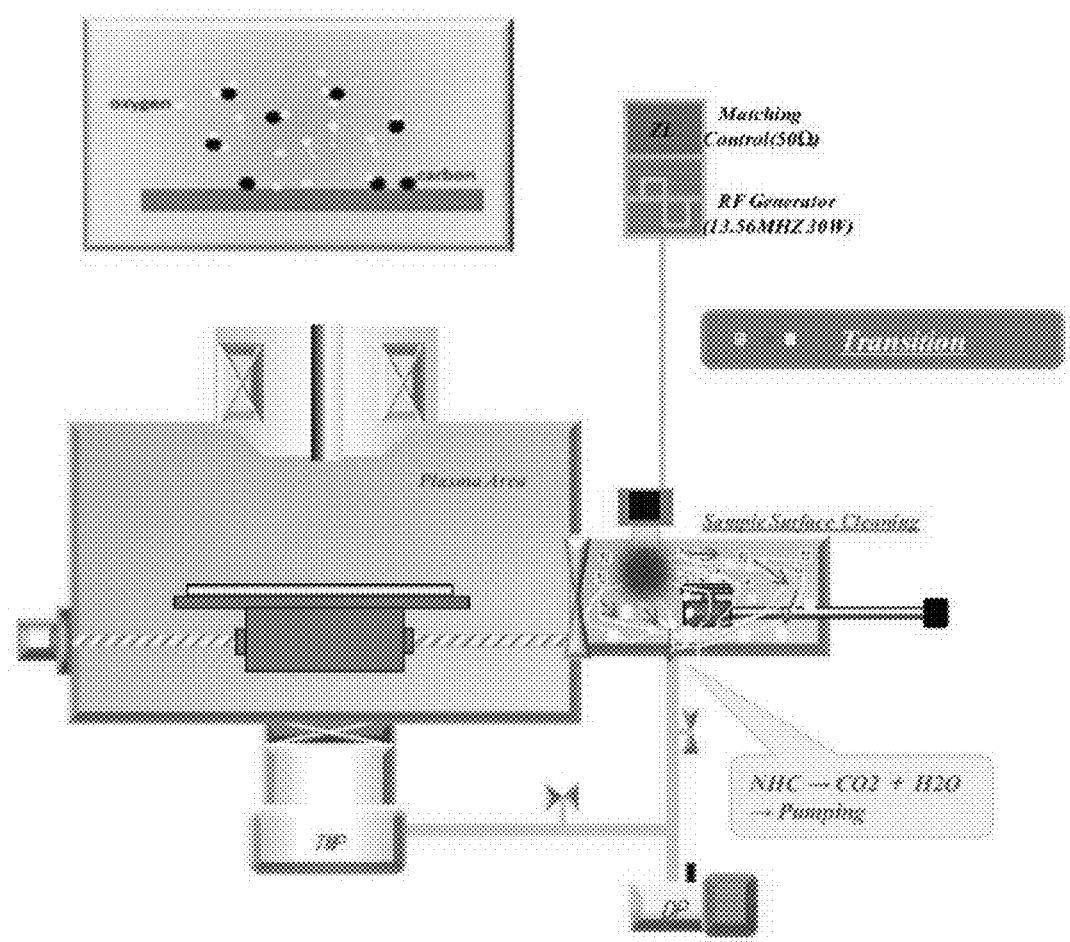
FIG. 8 shows the sample surface cleaning principle of a sample exchange chamber (SEC)-mounted type electron microscope plasma cleaner according to the present invention.
Figure 9:
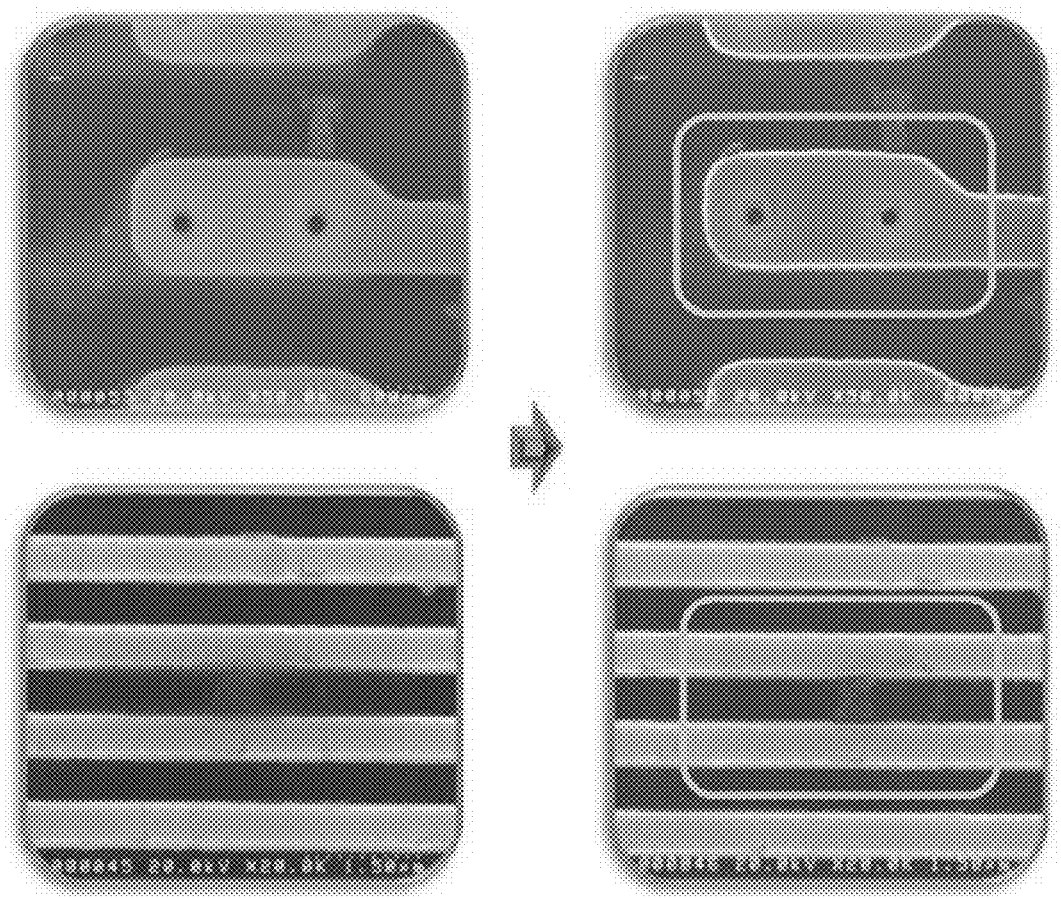
FIG. 9 shows the comparison of result data on the sample surface before and after the electron microscope plasma cleaner of FIG. 8 is applied.

FIG. 8 shows the sample surface cleaning principle of a sample exchange chamber (SEC)-mounted type electron microscope plasma cleaner according to the present invention, and FIG. 9 shows the comparison of result data on the sample surface before and after the electron microscope plasma cleaner of FIG. 8 is applied.

Referring to FIG. 8, the contaminants on the surface of the sample are cleaned (within about 5 minutes), without stopping a TMP (turbomolecular pump), in the sample exchange chamber, before the sample is introduced into the sample chamber.

As shown, if the gate valve is locked after the plasma head is mounted on the sample exchange chamber, the contaminated organics on the surface of the sample are cleaned.

Since only a low vacuum pump is connected to the sample exchange chamber, the surface of the sample can be cleaned within rapid time, without stopping the TMP.

The contaminants on the surface of the general semiconductor sample can be cleaned within 5 minutes.

After the TMP stops, further, if the gate valve is open to conduct the plasma cleaning, oxygen radicals and ions move to the sample chamber to clean the contaminants in the sample chamber, but it is hard to penetrate the flow of gas into the interior of the sample chamber, so that the cleaning time is longer than that when the plasma head is mounted on the sample chamber, which lowering the cleaning efficiency.

So as to remove such problems, accordingly, a plasma head for cleaning the sample chamber is additionally mounted.

Referring to FIG. 9, it can be checked that the data located on the right side as the data after the cleaning is more vivid than that located on the left side in the image data for the organic absorption layer.

Figure 10:
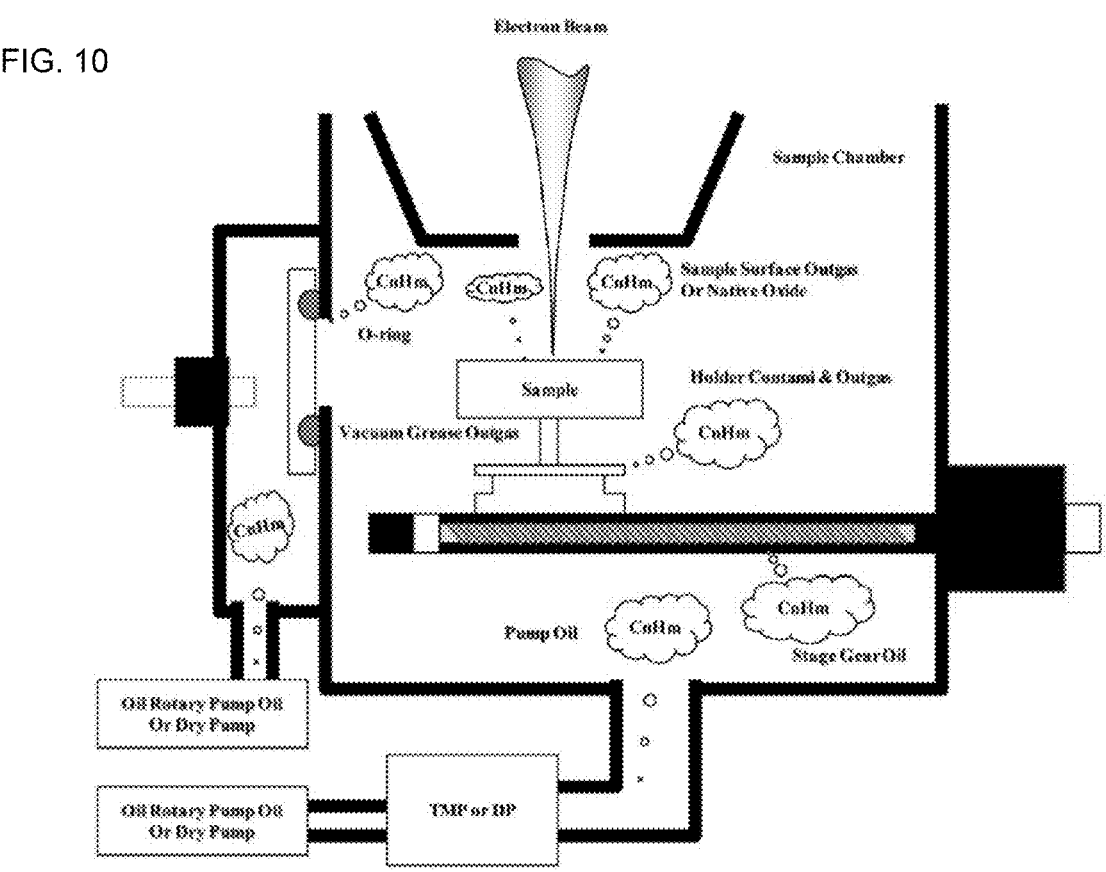
FIG. 10 shows the sample surface cleaning principle of a sample chamber (SC)-mounted type electron microscope plasma cleaner according to the present invention.

On the other hand, FIG. 10 shows the sample surface cleaning principle of a sample chamber (SC)-mounted type electron microscope plasma cleaner according to the present invention.

Figure 11:
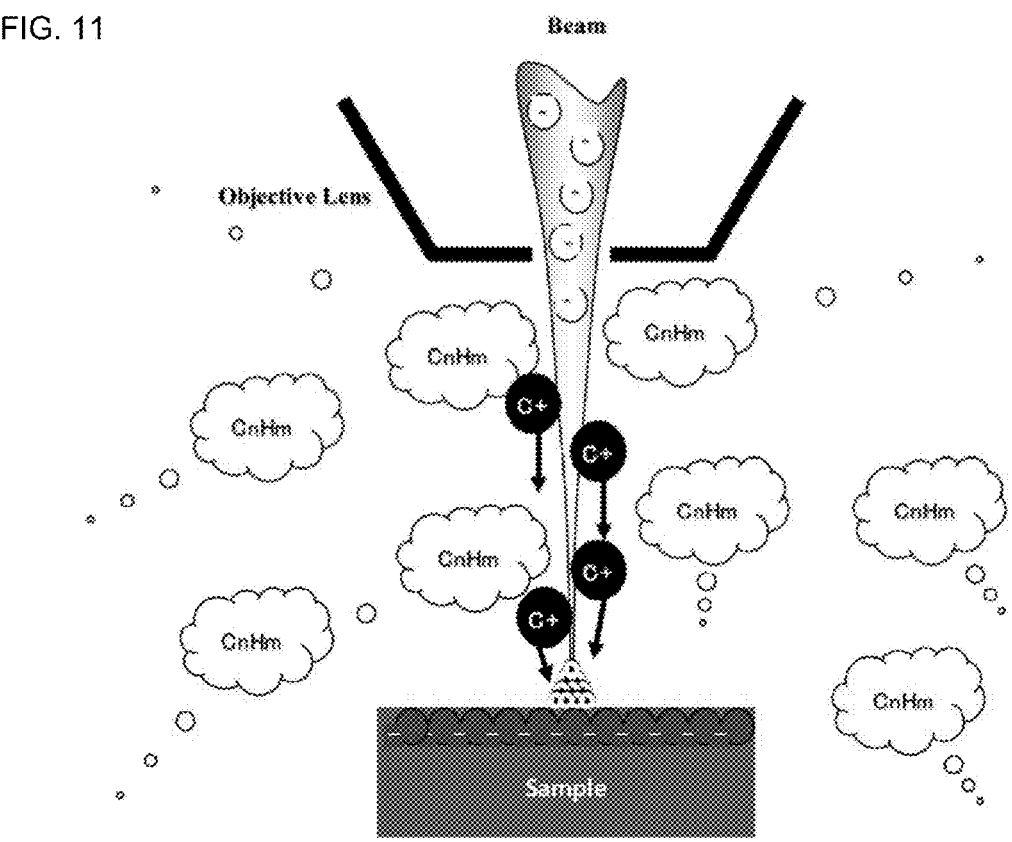
FIG. 11 shows the contamination in the sample chamber of FIG. 10.

Further, FIG. 11 shows the contamination in the sample chamber of FIG. 10.

Figure 12:
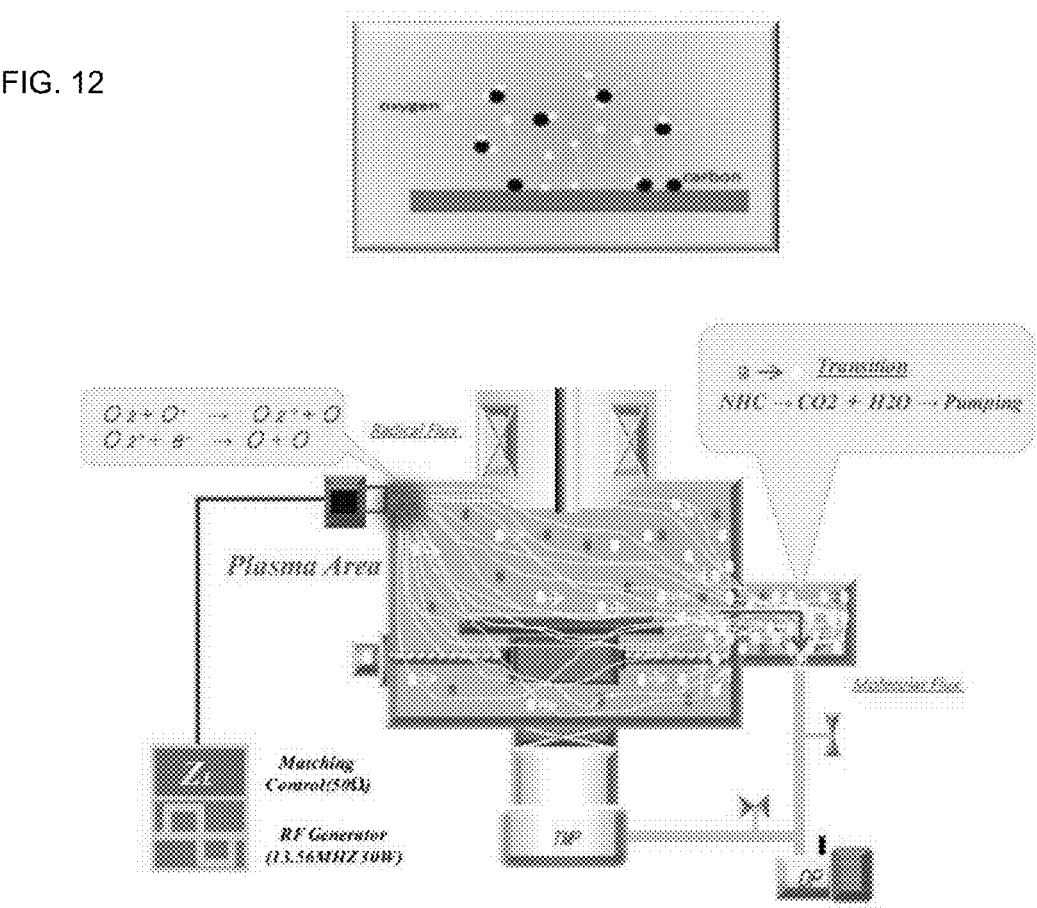
FIG. 12 additionally shows the sample surface cleaning principle of the sample chamber (SC)-mounted type electron microscope plasma cleaner according to the present invention.

FIG. 12 additionally shows the sample surface cleaning principle of the sample chamber (SC)-mounted type electron microscope plasma cleaner according to the present invention.

Figure 13:
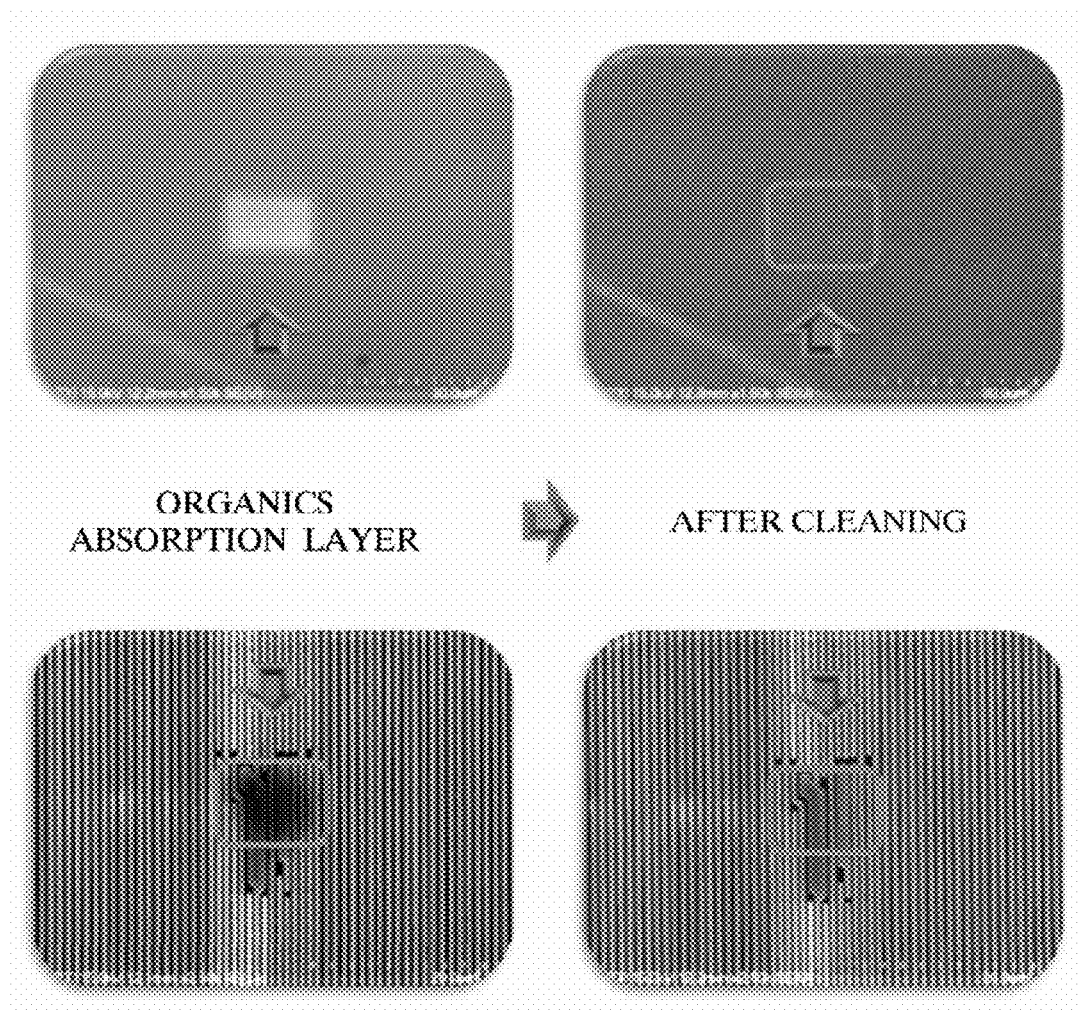
FIG. 13 the comparison of result data on the sample surface before and after the electron microscope plasma cleaner of FIGS. 10 to 12 is applied.

FIG. 13 the comparison of result data on the sample surface before and after the electron microscope plasma cleaner of FIGS. 10 to 12 is applied.

Referring first to FIG. 10, various image interference sources exist in the interior of the sample chamber of the analyzer like FE-SEM due to the organic molecules such as hydrocarbons.

That is, as shown in FIG. 11, contaminants occur in the sample chamber.

At this time, as shown in FIG. 12, the sample chamber-mounted type vacuum chamber cleaning principle is applied. In more detail, in the state where only a dry pump is activated after the TMP stops, the organics existing in the sample chamber are cleaned (for 1 to 2 hours) by using the radicals and ions.

Referring to FIG. 12, the oxygen radicals and ions produced from the plasma head are bonded to organic molecules absorbed/desorbed or moving in the sample chamber, without being pumped, and thus activated to gas such as $CO_2$ or $H_2O$. Next, the gas is pumped in the pumping direction.

In case of the sample chamber-mounted type electron microscope plasma cleaner, further, the pressure of the plasma cleaning $\cong 6\times 10^{-1}$ Torr, so that after the TMP stops, only the low vacuum pump like a dry pump or a rotary pump is operated to conduct the cleaning operation.

Generally, the cleaning is conducted for 1 to 2 hours.

Referring to FIG. 13, further, it can be checked that the data located on the right side as the data after the cleaning is more vivid than that located on the left side in the image data for the organic absorption layer.

Figure 14A:
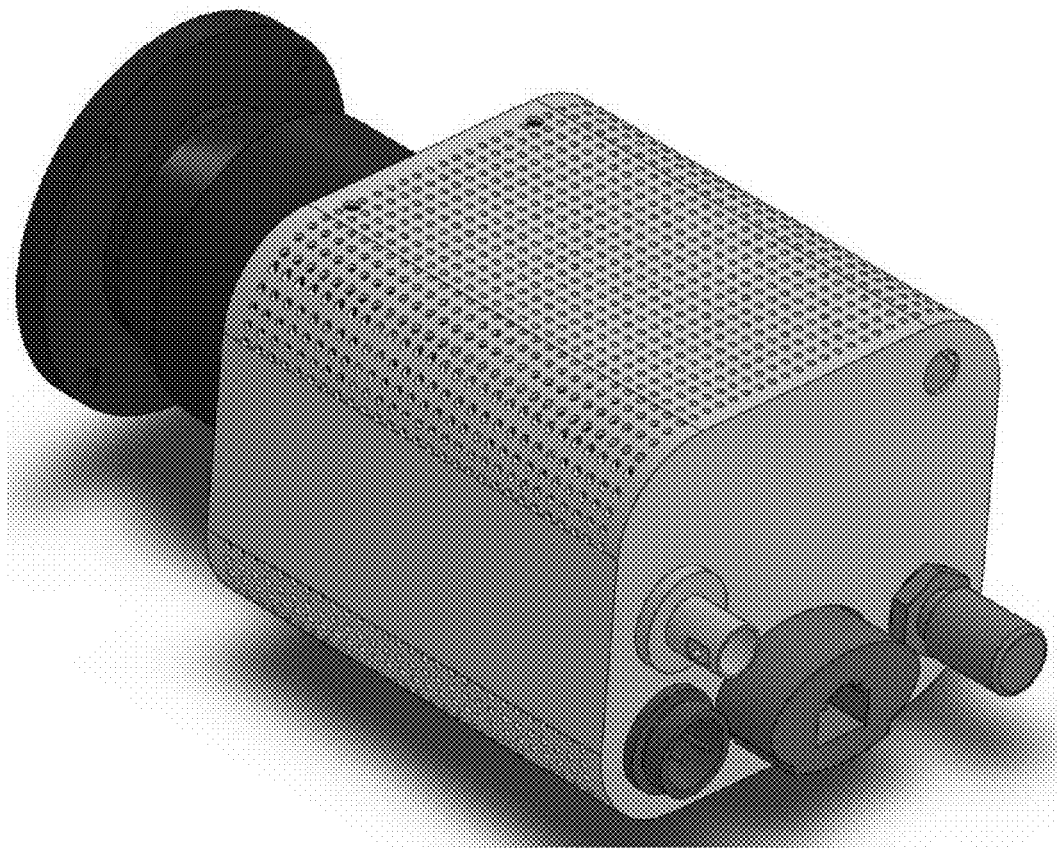
FIGS. 14a and 14b show a plasma head adopted in the present invention.
Figure 14B:
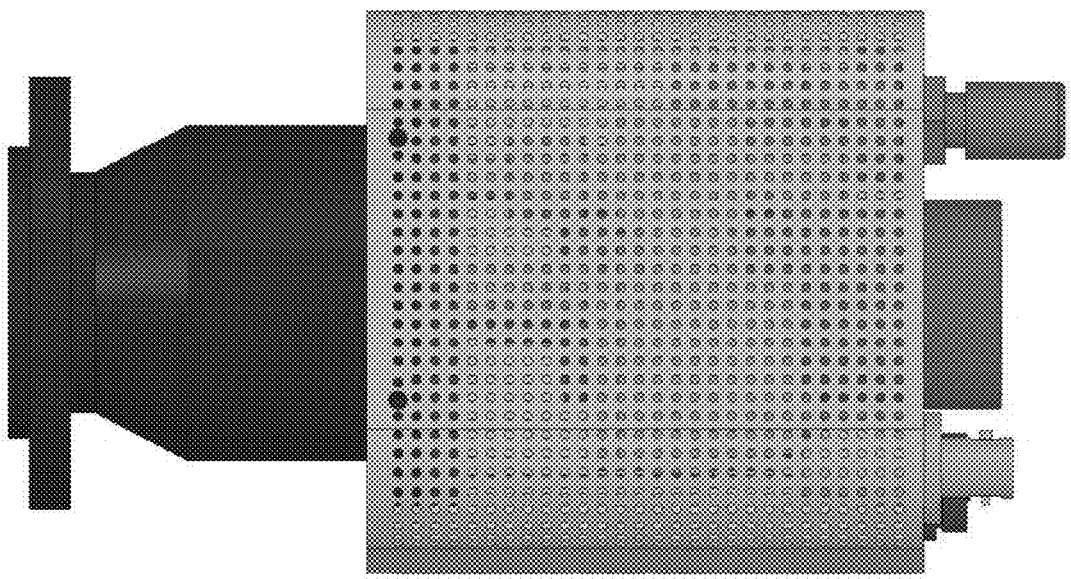

On the other hand, FIGS. 14a and 14b show the plasma head adopted in the present invention.

Referring to FIGS. 14a and 14b, a high efficiency triple-cup plasma source is shown on the front surface of the plasma head, and as the external components of the plasma head, a DC24V valve controller, an RF power (BNC port), a Pirani gauge (LAN port), a gas inlet (air or $O_2$), and a needle valve (manual) are shown.

Figure 15A:
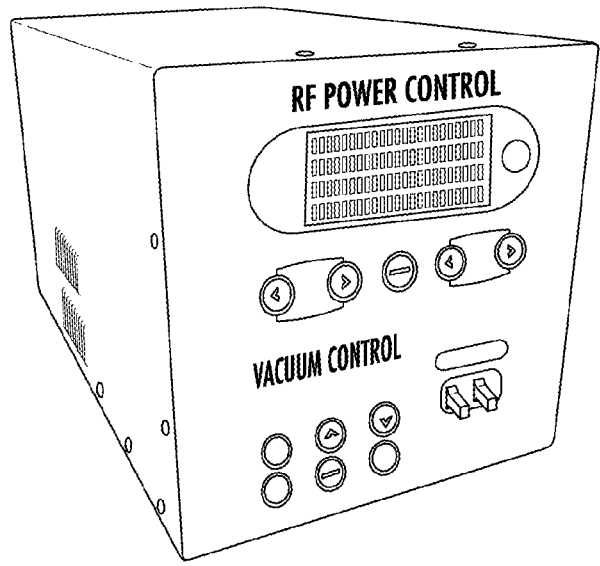
FIGS. 15a to 15c show one example of an RF power controller adopted in the present invention.
Figure 15B:
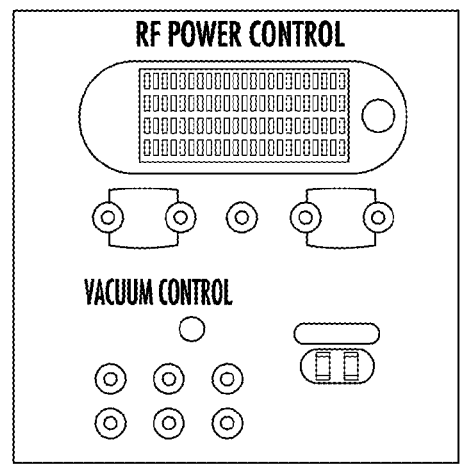
Figure 15C:
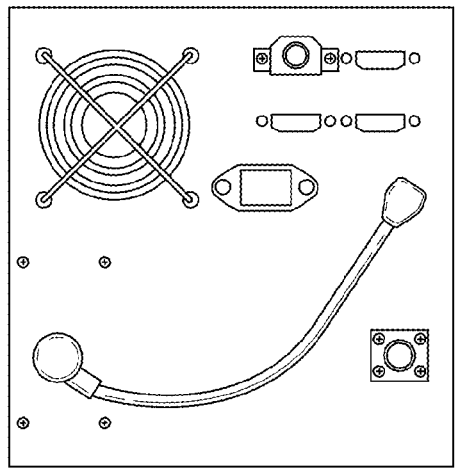

FIGS. 15a to 15c show one example of an RF power controller adopted in the present invention.

FIG. 15a shows the whole shape of the RF power controller adopted in the present invention, FIG. 15b shows the front surface thereof, and FIG. 15C shows the rear surface thereof.

The RF power controller is a device supplying a high frequency of 13.56 MHz/10 to 30 W (Max 40 W), wherein the cleaning process is programmed therein and automatically conducted.

FIGS. 16a to 16c show a cable set according to the present invention.

FIG. 16a shows the whole cable set, FIG. 16b shows the head assembly thereof, and FIG. 16C shows the controller thereof.

So as to raise the cleaning effects according to the present invention, further, the following environments should be desirably given.

That is, since a high frequency generator according to the present invention is designed used indoors at a height of 2,000 m or less, desirably, the variation width of alternating voltage is ±10% of specification, the temperature in the installation place is in the range between 5° C. and 35° C., the relative humidity in the installation place is 80% or under, the installation place does not have any dust, solution, and acid steam, and the installation place is not vibrated.

Figure 17:
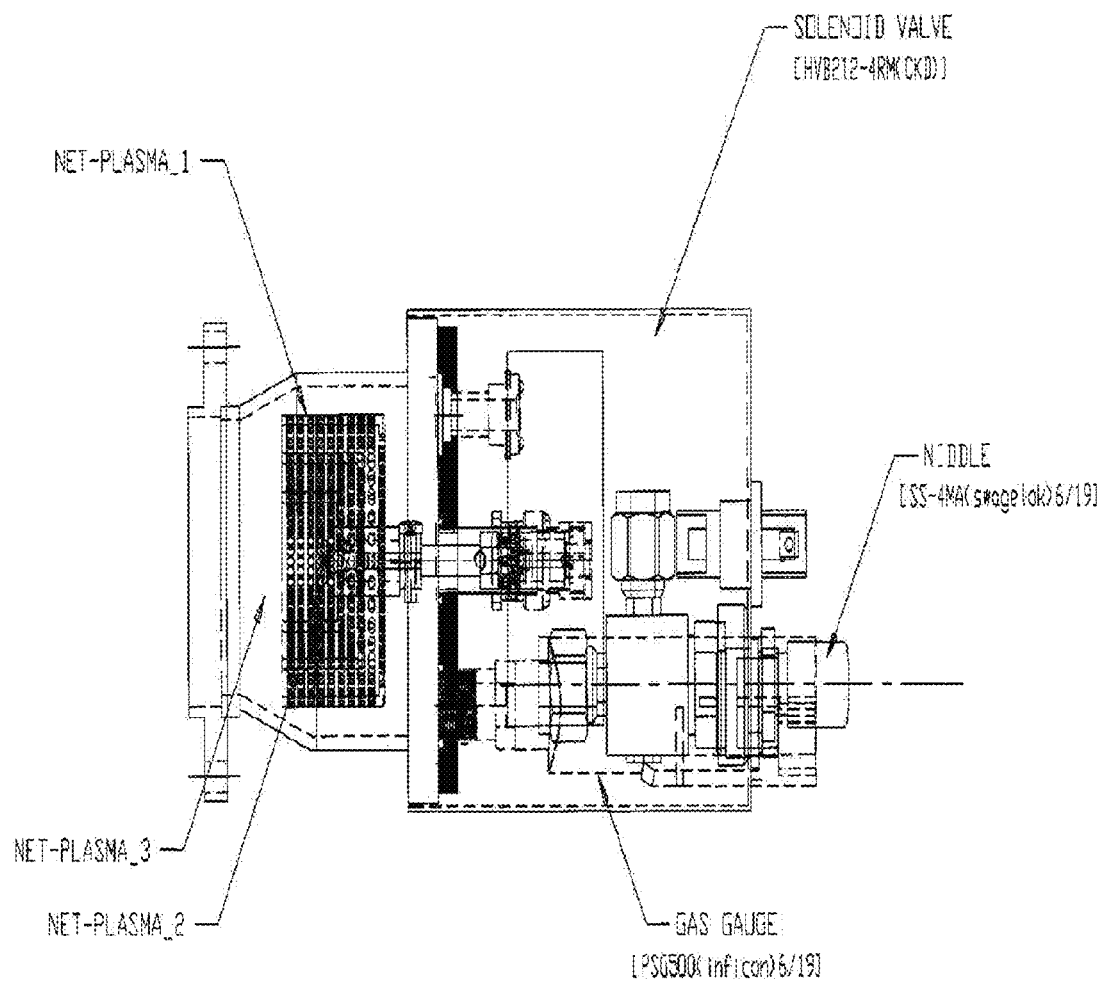
FIG. 17 shows the internal configuration of the plasma head according to the present invention.

On the other hand, FIG. 17 shows the internal configuration of the plasma head according to the present invention.

Referring to FIG. 17, the detailed configurations of the triple cup plasma electrode, a multi gas nozzle, solenoid valve, RF application feed-through, micro needle valve, and Pirani gauge are shown.

Figure 18A:
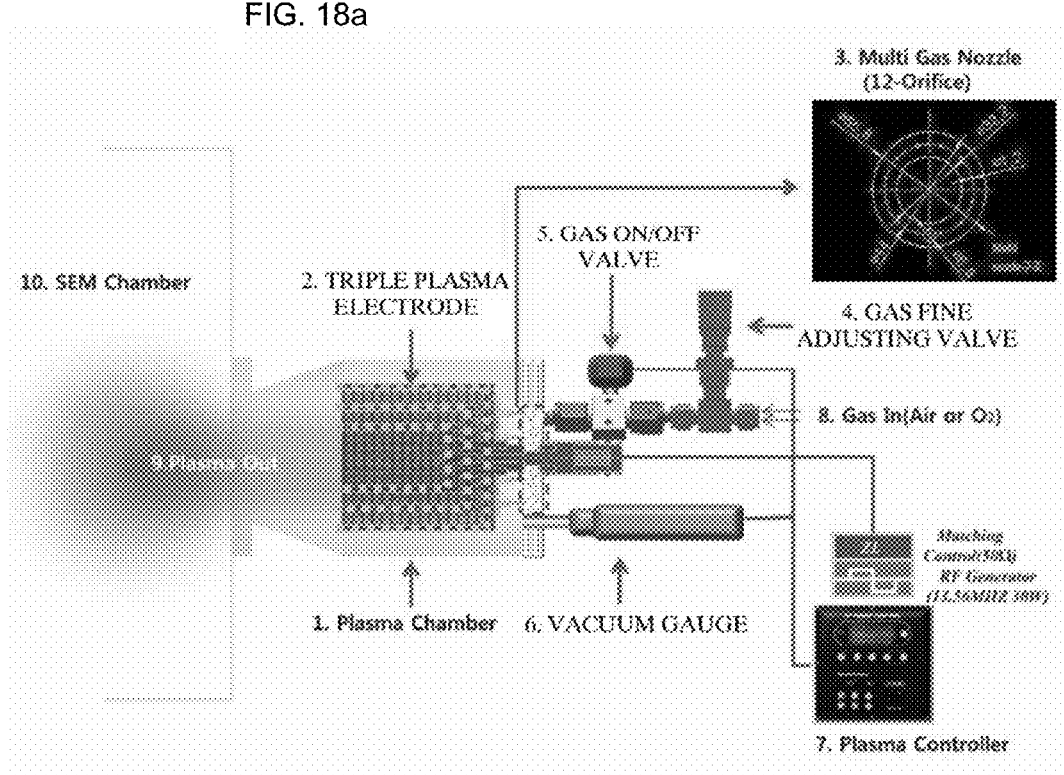
FIGS. 18a and 18b show the operating way of the plasma head according to the present invention.
Figure 18B:
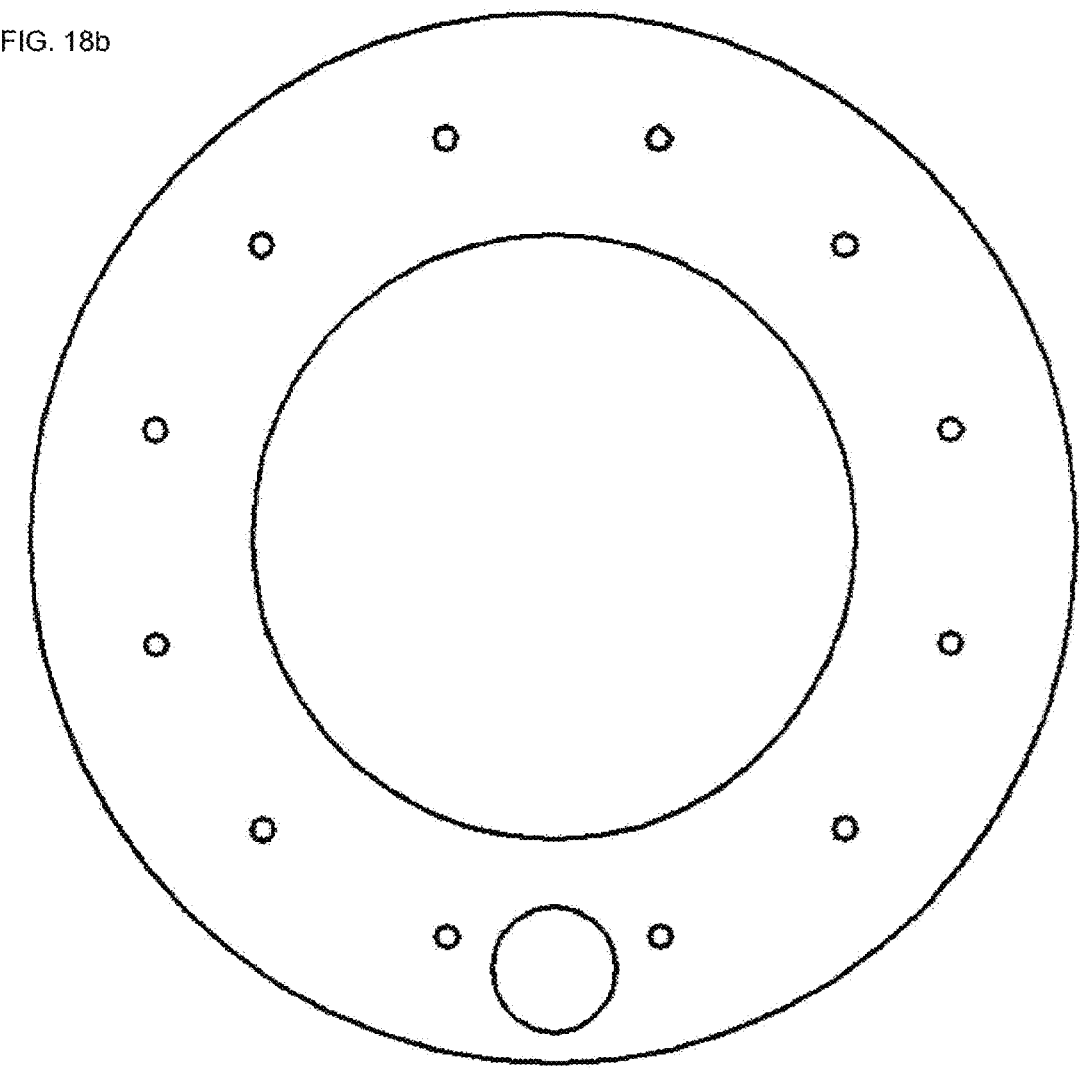

FIGS. 18*a* and 18*b* show the operating way of the plasma head according to the present invention.

Referring to FIG. 18*a*, the plasma chamber, plasma electrode (triple structure), multi gas nozzle, gas fine adjusting valve, gas on/off valve, vacuum gauge, plasma controller, gas inlet (air or $O_2$), plasma outlet, and SEM chamber are in detail illustrated.

Referring to FIG. 18*b*, the detailed information on the 12-orifices of the multi gas nozzle is shown.

In more detail, before the plasma cleaning is conducted, the vacuum chamber of the SEM and any other analyzing vacuum device is pumped just by means of the low vacuum pump (for example, dry pump, oil rotary pump and the like).

The valve of the high vacuum pump such as the TMP or diffusion pump is closed. If the valve is not mounted on the pump, the operation of the pump stops.

Further, in the state where the vacuum chamber of the object device for the plasma cleaning is pumped by means of the low vacuum pump (<1 Pa pump), the main power of the plasma controller is turned on, and if the pressure of the chamber is under 8×10−1 Torr, the power is automatically applied to the gas on/off valve, thus opening the valve.

If the pressure of the chamber does not reach 8×10−1 Torr, the high frequency is not applied from the plasma controller.

The gas fine adjusting valve is adjusted to a pressure within the range between 5×10−1 Torr and 7×10−1 Torr.

At this time, the air or $O_2$ gas introduced from the gas inlet is evenly injected to the plasma electrode through the 12-orifices of the multi gas nozzle.

Vacuum reading is recognized by means of the vacuum gauge and displayed on the plasma controller, and accordingly, the vacuum display mounted on the device to be cleaned is ignored, while referring to the numeric value displayed on the plasma controller.

The gas fine adjusting valve does not change the quantity of gas introduced thereinto unless the valve is separately adjusted after initially adjusted, so that if the pressure at next cleaning is not escaped from the allowable pressure, no adjustment is needed.

If the pressure of the chamber is within the allowable pressure, a high frequency of 13.56 MHz/10 to 40 W is applied from the plasma controller to the triple cup plasma source of the plasma electrode.

At this time, plasma is generated from the plasma electrode.

The gas is evenly injected into the triple structured plasma electrode through the 12 orifices of the multi gas nozzle, thus optimizing the efficiency of the generation of the plasma.

The oxygen radicals (O) and oxygen ions (O+), which are ionized and activated by means of the plasma generated from the plasma electrode, are produced and enter the object to be cleaned.

The oxygen radicals and oxygen ions are bonded to organics (hydrocarbons) on the chamber or the surface of the sample inside the object to be cleaned and activated to $CO_2$ or $H_2O$. Next, the gas is pumped and removed by means of the pump of the object to be cleaned.

In case of the sample chamber, the cleaning is conducted for 1 to 3 hours according to the volumes of the sample chamber, and in case of the surface of the sample for observation and analysis, the cleaning is conducted for tens of seconds to 10 minutes according to the kinds of the sample.

If the cleaning is finished, the radio frequency applied from the plasma controller is turned off and the gas on/off valve is closed.

After that, if the pumping for the vacuum required for the object to be cleaned is finished, high resolution image having no organic contamination can be acquired and precisely analyzed.

On the other hand, the triple cup plasma source as one of the main characteristics of the present invention can be used.

FIGS. 19*a*, 19*b*, 19*c* and 19*d* show a triple cup plasma source proposed according to the present invention.

Figure 19A:
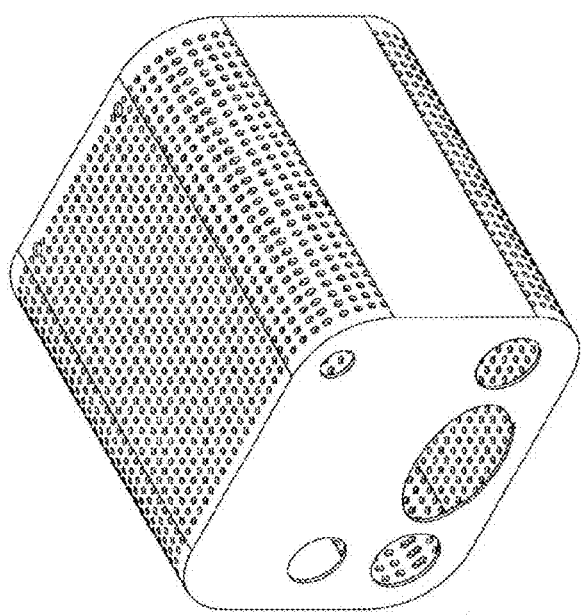
FIGS. 19a, 19b, 19c and 19d show a triple cup plasma source proposed according to the present invention.
Figure 19B:
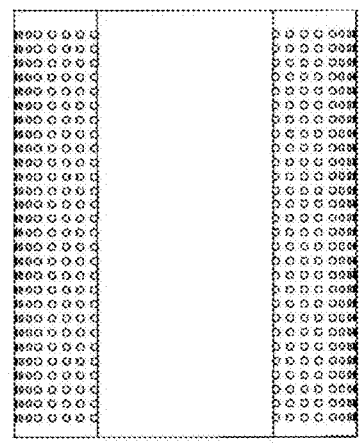
Figure 19C:
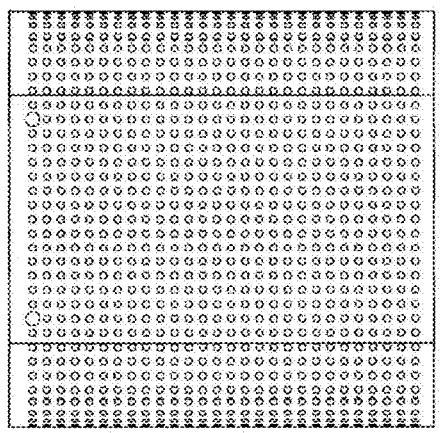
Figure 19D:
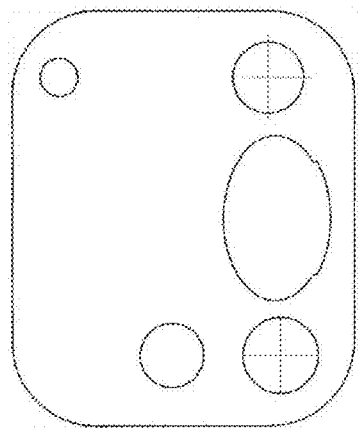

FIG. 19*a* shows the outer shape of the plasma source, and FIG. 19*b* shows the internal structure of the plasma source.

Referring to FIGS. 19*a*, 19*b*, 19*c* and 19*d*, the plasma electrode has a shape of a triple cup and forms multi holes (2 mm) on all surfaces thereof, thus maximizing the reaction area with the plasma producing gas.

Accordingly, the loss rate of the ionization of the gas can be minimized and the efficiency of the generation of the plasma can be maximized.

The cleaning efficiency and the charging removal efficiency can be obtained higher two times than those in the existing product.

Figure 20A:
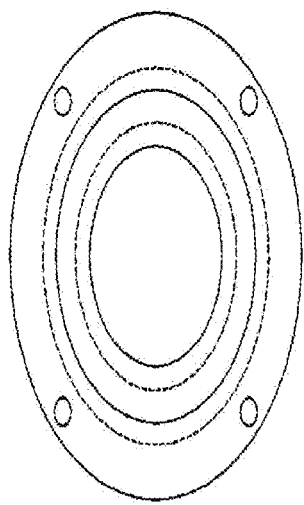
FIGS. 20a, 20b and 20c show an example of a multi gas nozzle according to the present invention.
Figure 20B:
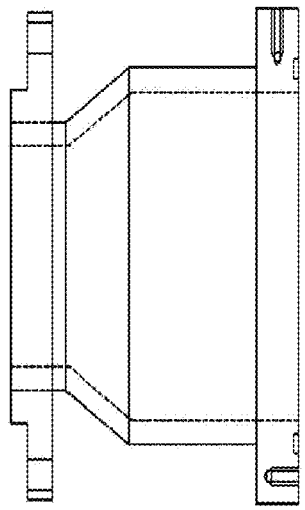
Figure 20C:
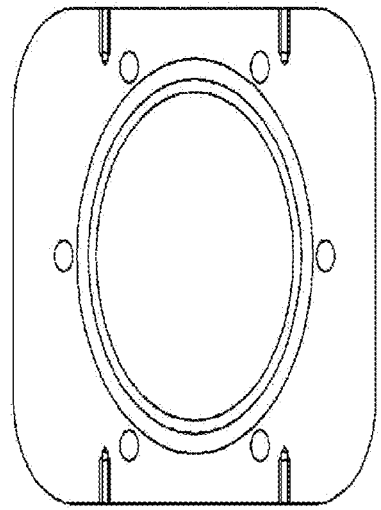

On the other hand, FIGS. 20*a*, 20*b* and 20*c* show an example of a multi gas nozzle according to the present invention.

FIG. 20*a* shows the structure of the multi gas nozzle and FIG. 20*b* shows the gas flowing direction.

Referring to FIGS. 20*a*, 20*b* and 20*c*, since the existing product just injects the plasma gas from the center portions of the side surfaces thereof, it does not distribute the plasma gas on the plasma electrode evenly. Accordingly, the plasma gas is introduced into the side portions of the plasma electrode, thus making the efficiency of the generation of the plasma deteriorated.

Contrarily, the multi gas nozzle of the present invention has an even injection structure over the whole surface of the plasma electrode.

That is, the multi gas injection nozzle having the 12 orifices (Φ1 mm) is mounted on the gas inlet (the rear end of the plasma electrode), thus allowing gas to collide against the whole surface of the plasma electrode to obtain the efficiency of the generation of the plasma to a maximum degree upon the application of high frequency, so that the cleaning efficiency and the charging removal efficiency can be obtained higher two times than those in the existing product.

Figure 21:
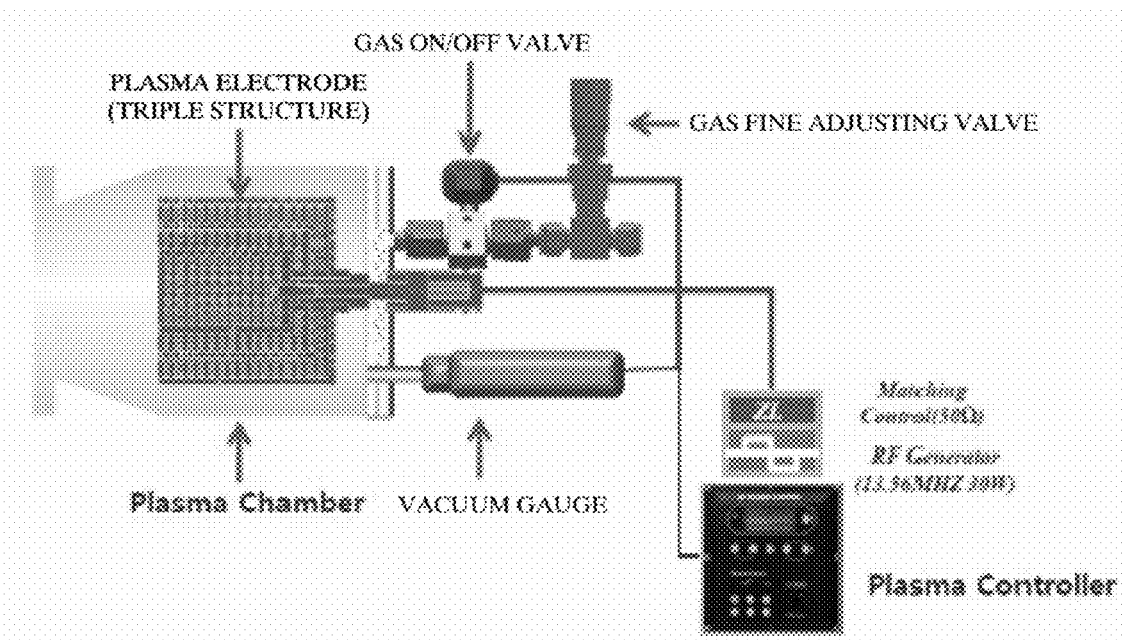
FIG. 21 shows the miniaturization and full auto control according to the present invention.

On the other hand, FIG. 21 shows the miniaturization and full auto control according to the present invention.

Referring to FIG. 21, additional devices (vacuum gauge, gas on/off valve, RF application feed-through, gas fine adjusting valve and the like) for plasma control are disposed on the rear end of the plasma head, thus minimizing the diameter and size of the plasma head.

Accordingly, the restrictions caused by the plasma head size in mounting the plasma head on the object to be cleaned can be improved, and all control signals are connected to the rear end of the plasma head, thus making the connection cables simplified in installation.

After the cleaning pressure control of the object to be cleaned, the RF on/off, and cleaning are all finished, the pumping start of the object to be cleaned is programmed on the plasma controller, thus making the whole process of the cleaning automatically conducted.

According to the present invention, the plasma cleaning time can be reduced. That is, the density of plasma generated from the plasma source is higher than that in the existing product, thus allowing the cleaning time to be substantially shortened.

According to the present invention, next, the plasma head can be miniaturized. In case of the existing product, the control parts of the plasma head are disposed on the side surface thereof, which causes the restrictions in the mounting thereof. Accordingly, the existing plasma head is mounted only on the sample chamber and not mounted on the sample exchange chamber, thus making it impossible to clean the surface of the sample. According to the present invention, contrarily, all control parts of the plasma head are disposed on the rear end thereof, which makes the plasma head mounted on both of the sample chamber and the sample exchange chamber, without any restriction.

According to the present invention, further, the surface of the sample of the object to be cleaned can be cleaned. Since the existing product is mounted only on the sample chamber, the surface of the sample is cleaned in the state where the high vacuum pump stops or shuts off, so that the cleaning should be conducted for at least three hours or more. Accordingly, the existing product cannot be used for cleaning the surface of the sample. According to the present invention, contrarily, the cleaner according to the present invention is mounted on the sample exchange chamber, and therefore, after the cleaning of the interior of the sample exchange chamber, the cleaner is just loaded to the sample chamber, without stopping or separately shutting off the high vacuum pump, thus conducting the observation and analysis.

According to the present invention, furthermore, the charging removal effects of the wafer, LCD, and chamber structure can be obtained. That is, large quantities of radicals and positive ions are produced from the plasma source when the present invention is used for semiconductors and LCD in-line equipment and injected into the chamber, thus effectively removing the charging causing various defects.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. An electron microscope plasma cleaner for cleaning an electron microscope by using plasma, the electron microscope adapted to magnify an image of a sample through an electron beam, the electron microscope plasma cleaner comprising:
    a vacuum chamber in which the sample is disposed, the interior of the vacuum chamber being in a vacuum state to utilize electron current;
    an electron gun for producing the electron beam and outputting the produced electron beam to the sample;
    an electron lens for magnifying the electron beam transmitting the sample and projecting the electron beam onto a fluorescent screen;
    a radio frequency controller for producing a first signal having radio frequency within a given range; and
    a plasma head for producing the plasma, receiving the first signal from the radio frequency controller, producing activated oxygen radicals and ions by using the plasma and the first signal, and supplying the activated oxygen radicals and ions to the interior of the vacuum chamber,
    wherein contaminants existing in the interior of the vacuum chamber are removed with the activated oxygen radicals and ions supplied to the interior of the vacuum chamber,
    wherein the contaminants comprise hydrocarbons, native oxide formed when the sample is kept in the air, oil, and sample outgas,
    wherein at least one of the activated oxygen radicals and ions reacts to the contaminants to produce $H_2O$ or $CO_2$,
    wherein the contaminants are discharged to the outside of the vacuum chamber by using motion energy becoming high by means of the production of $H_2O$ or $CO_2$,
    wherein the ions supplied to the interior of the vacuum chamber are bonded to the static electricity formed on the vacuum chamber and the sample, thus removing the static electricity,
    wherein the vacuum chamber is a sample exchange chamber (SEC),
    wherein the contaminants comprise one of native oxide formed when the sample disposed in the sample exchange chamber (SEC) is kept in the air, oil, and sample outgas,
    wherein the plasma head comprises a plasma electrode having a plurality of cups laid on each other, each cup having a plurality of holes formed on every surface thereof, so that the reaction area with a first gas producing the plasma is maximized through the plurality of cups and the plurality of holes, and
    wherein the plasma head comprises a multi gas injection nozzle disposed on the front surface thereof to inject the first gas therefrom, thus assisting the production of the plasma.

2. The electron microscope plasma cleaner according to claim 1, wherein the contaminants having high motion energy are discharged to the outside of the vacuum chamber by means of the pumping operation of a vacuum pump.

3. The electron microscope plasma cleaner according to claim 1, wherein the electron microscope comprises one of a transmission electron microscope (TEM), a scanning electron microscope (SEM), a scanning transmission electron microscope (STEM), and an X-ray micro analyzer (EFMA or XMA).

4. A method for cleaning an electron microscope by using plasma, the electron microscope adapted to magnify an image of a sample through an electron beam, the method comprising the steps of:
    disposing the sample in an interior of a vacuum chamber being in a vacuum state to utilize electron current;
    producing the electron beam through an electron gun;
    outputting the produced electron beam to the sample;
    magnifying the electron beam transmitting the sample through an electron lens and projecting the electron beam onto a fluorescent screen;
    producing a first signal having radio frequency within a given range from a radio frequency controller;
    producing the plasma through a plasma head;
    receiving the first signal from the radio frequency controller through the plasma head;
    producing activated oxygen radicals and ions from the plasma head by using the plasma and the first signal; and
    supplying the activated oxygen radicals and ions from the plasma head to the interior of the vacuum chamber,
    wherein contaminants existing in the interior of the vacuum chamber are removed with the activated oxygen radicals and ions supplied to the interior of the vacuum chamber,
    wherein the contaminants comprise hydrocarbons, native oxide formed when the sample is kept in the air, oil, and sample outgas,
    wherein at least one of the activated oxygen radicals and ions reacts to the contaminants to produce $H_2O$ or $CO_2$,
    wherein the contaminants are discharged to the outside of the vacuum chamber by using the motion energy becoming high by means if the production of $H_2O$ or $CO_2$,
    further comprising the step of bonding the ions supplied to the interior of the vacuum chamber to static electricity formed on the vacuum chamber and the sample and removing the static electricity, wherein the vacuum chamber is a sample exchange chamber (SEC), wherein the contaminants comprises one of native oxide formed when the sample disposed in the sample exchange chamber (SEC) is kept in the air, oil, and sample outgas, wherein the plasma head comprises a plasma electrode having a plurality of cups laid on each other, each cup having a plurality of holes formed on every surface thereof, so that the reaction area with a first gas producing the plasma is maximized through the plurality of cups and the plurality of holes, and wherein the plasma head comprises a multi gas injection nozzle disposed on the front surface thereof to inject the first gas therefrom, thus assisting the production of the plasma.

5. The method according to claim 4, wherein the contaminants having high motion energy are discharged to the outside of the vacuum chamber by means of the pumping operation of a vacuum pump.

6. The method according to claim 4, wherein the electron microscope comprises one of a transmission electron microscope (TEM), a scanning electron microscope (SEM), a scanning transmission electron microscope (STEM), and an X-ray micro analyzer (EFMA or XMA).

\* \* \* \* \*